(12) United States Patent
Berna et al.

(10) Patent No.: US 7,615,047 B2
(45) Date of Patent: Nov. 10, 2009

(54) LASER TIP INCISION TEMPLATE FOR BONE SURGERY

(75) Inventors: Norberto Berna, Via D. Macaluso, 23, 00146 Roma (IT); Vincenzo Crudo, Arzignano (IT)

(73) Assignee: Norberto Berna, Rome (IT)

( * ) Notice: Subject to any disclaimer, the term of this patent is extended or adjusted under 35 U.S.C. 154(b) by 763 days.

(21) Appl. No.: 10/843,476

(22) Filed: May 12, 2004

(65) Prior Publication Data

US 2004/0249370 A1     Dec. 9, 2004

(30) Foreign Application Priority Data

May 15, 2003     (IT) .......................... PD2003A0102

(51) Int. Cl.
*A61B 17/00* (2006.01)
(52) U.S. Cl. ................. 606/1; 606/63; 606/80; 433/29; 433/53
(58) Field of Classification Search ............ 606/1, 606/53, 79, 80; 433/25, 29, 53; 600/160, 600/178
See application file for complete search history.

(56) References Cited

U.S. PATENT DOCUMENTS

| | | | | |
|---|---|---|---|---|
| 3,297,022 A * | 1/1967 | Wallace ...................... 600/172 |
| 4,170,997 A * | 10/1979 | Pinnow et al. ................. 606/3 |
| 4,367,729 A * | 1/1983 | Ogiu .......................... 600/108 |
| 4,438,773 A * | 3/1984 | Letterio ...................... 600/561 |
| D342,136 S * | 12/1993 | Lafferty et al. ............. D24/138 |
| 5,527,182 A * | 6/1996 | Willoughby ................. 433/172 |
| 5,647,840 A * | 7/1997 | D'Amelio et al. ........... 600/169 |
| 5,718,664 A * | 2/1998 | Peck et al. ................... 600/178 |
| 5,833,701 A * | 11/1998 | Gordon ...................... 606/166 |
| 5,990,382 A * | 11/1999 | Fox .......................... 623/16.11 |
| 6,210,355 B1 | 4/2001 | Bek et al. |
| 6,267,769 B1 | 7/2001 | Truwit |
| 6,342,053 B1 * | 1/2002 | Berry ............................. 606/5 |
| 2001/0014771 A1 | 8/2001 | Liu et al. |

\* cited by examiner

*Primary Examiner*—Ahmed M Farah
(74) *Attorney, Agent, or Firm*—Stout, Uxa, Buyan & Mullins, LLP

(57) ABSTRACT

A shape and depth template for incisions with laser tips, usable in bone surgery, comprising a guiding body for a laser tip provided with two mutually opposite end faces arranged at a preset distance and a lateral surface, one of the end faces being arrangable at the laser tip incision region and with a hole that of preset shape that passes there through from one end face to the other.

15 Claims, 2 Drawing Sheets

LASER TIP INCISION TEMPLATE FOR BONE SURGERY

The present invention relates to a shape and depth template for incisions with laser tips, particularly usable in bone surgery.

The invention is used particularly but not exclusively for providing osteotomy sites for dental implants.

The invention can also be applied in the execution of bone biopsies, the removal of calibrated bone samples for the most disparate uses in orthopedics, et cetera.

BACKGROUND OF THE INVENTION

Until recently, the use of lasers in surgery was limited to the cutting of substantially soft tissues, since it was not possible to calibrate the power of the laser for harder tissues.

Generally, if these lasers were applied to bone portions, they would burn said portions, with consequent death of the component cells.

Recently, new developments in laser technologies have allowed to provide lasers that are able to perform incisions in bone tissues without burning them.

Scalpels with a laser tip are used for these incisions; the laser tips that are used can be different from one another: for example, the laser light of a laser tip can be conveyed by means of optical fibers or by means of waveguide systems, or by way of mirror systems; the laser of said scalpels may also be of the hydrokinetic type.

SUMMARY OF THE INVENTION

The aim of the present invention is to provide a shape and depth reference during the incision of biological tissues by means of laser tips.

Within this aim, an object of the present invention is to provide a shape and depth template for incisions with laser tips that is particularly usable in bone surgery.

Another object of the present invention is to provide a shape and depth template for incisions with laser tips, particularly usable in bone surgery, that allows easy operation on the part of the surgeon.

A further object of the present invention is to provide a shape and depth template for incisions with laser tips, particularly usable in bone surgery, that allows to provide osteotomy sites of extreme precision, which comply with the physiology of the affected region.

A still further object of the present invention is to provide a shape and depth template for incisions with laser tips, particularly usable in bone surgery, that allows to have a certain elasticity in choosing the shapes and dimensions of the sites to be provided.

Another object of the present invention is to provide a shape and depth template for incisions with laser tips, particularly usable in bone surgery, that can be produced with known systems and technologies.

This aim and these and other objects that will become better apparent hereinafter are achieved by a shape and depth template for incisions with laser tips that is particularly usable in bone surgery, characterized in that it comprises a guiding body for a laser tip that is delimited by two mutually opposite end faces arranged at a preset distance and by a lateral surface, one of said end faces being designed to be arranged at the region where incision with the laser tip is to be performed, said guiding body having a hole that has a preset shape and passes through it from one end face to the other.

BRIEF DESCRIPTION OF THE DRAWINGS

Further characteristics and advantages of the present invention will become better apparent from the following detailed description of a preferred but not exclusive embodiment thereof, illustrated by way of non-limiting example in the accompanying drawings, wherein.

DESCRIPTION OF THE PREFERRED EMBODIMENTS

Figure 1:
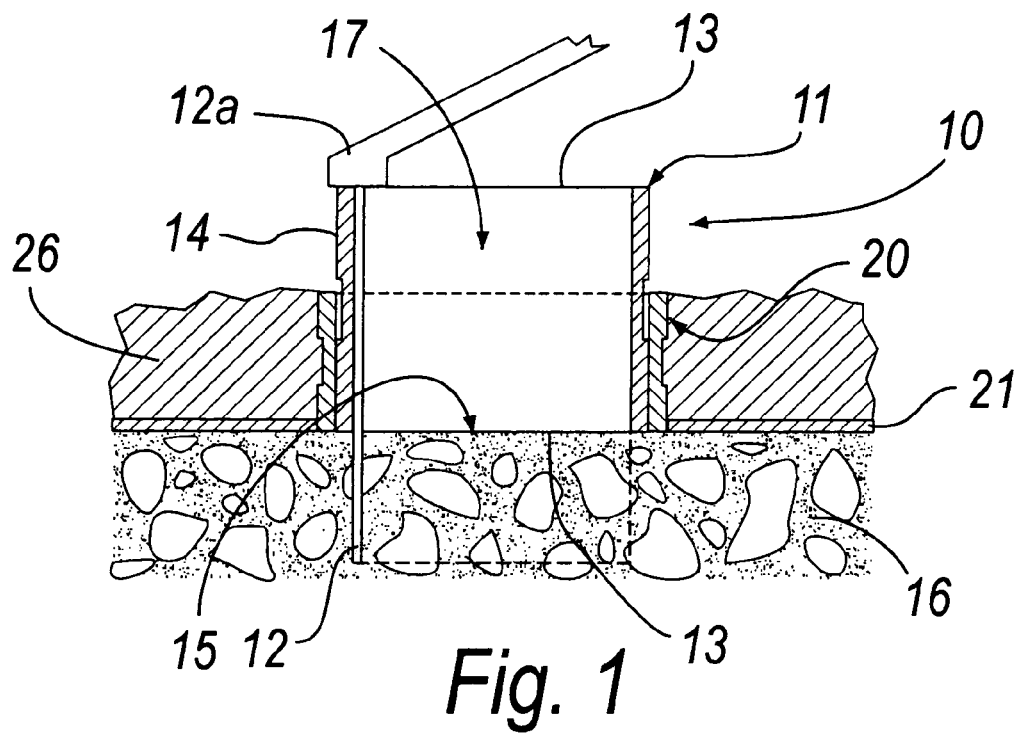
FIG. 1 is a sectional front view of a template according to the invention, applied to a gingival bone, illustrating a laser scalpel during incision.
Figure 2:
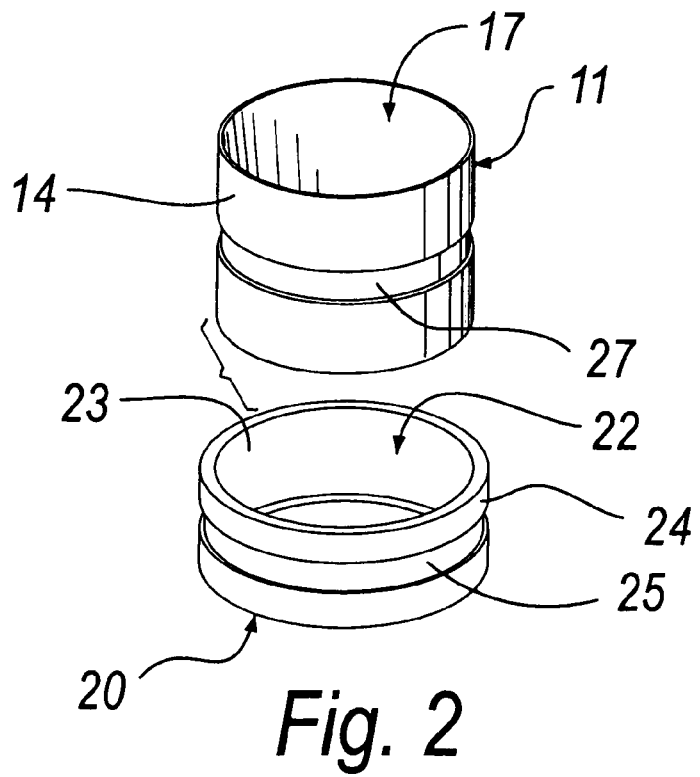
FIG. 2 is an exploded perspective view of a template according to the invention.

With reference to the figures, a shape and depth template for incisions with laser tips that is particularly usable in bone surgery according to the invention is generally designated by the reference numeral 10.

The template 10 comprises a guiding body 11 for a laser tip (of preset length), designated by the reference numeral 12 in FIG. 1.

The guiding body 11 is formed by two mutually opposite end faces 13, which are arranged at a standardized preset distance from each other, as will become better apparent hereinafter, and by a lateral surface 14.

One of the end faces 13 is to be arranged at a region 15 where incision with the laser tip 12 is to be performed.

For example, FIG. 1 illustrates a gingival bone 16 to which the template 10 according to the invention, useful for providing an osteotomy site for dental implants, is applied.

In this embodiment, the lateral surface 14 of the guiding body 11 has a substantially cylindrical shape.

The guiding body 11 has a hole 17 that has a preset shape and passes through it from one end face to the other.

In this embodiment, the hole 17, which is coaxial to the cylindrical extension of the entire guiding body 11, has a circular cross-section.

In other embodiments, shown in FIGS. 5 to 10, the hole 17 has a cross-section that is respectively triangular, elliptical, figure-of-eight (two-lobe), square, rectangular, semicircular, in all of which any corners are radiused.

Figure 3:
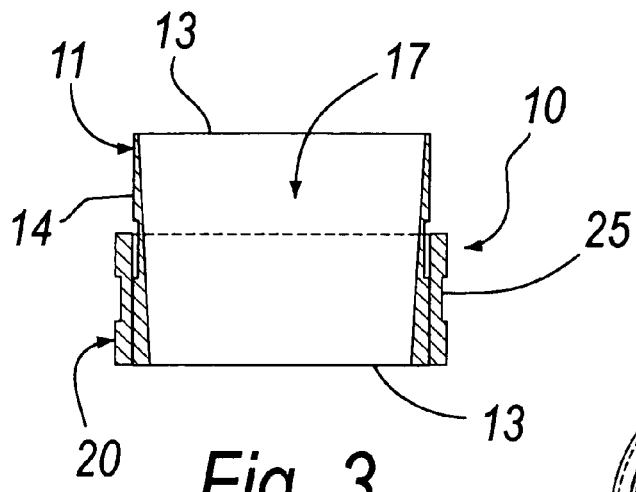
FIG. 3 is a sectional front view of a template according to the invention in an alternative embodiment with respect to the shape of FIG. 1.
Figure 4:
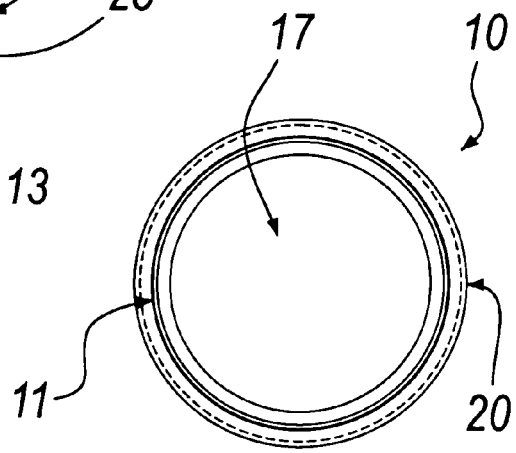
FIG. 4 is a plan view of the template of FIG. 3.
Figure 5:
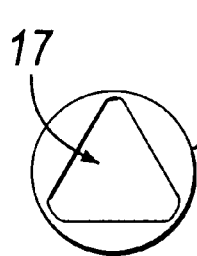
FIGS. 5 to 10 are five plan views of a corresponding number of alternative embodiments of the template according to the invention.
Figure 6:
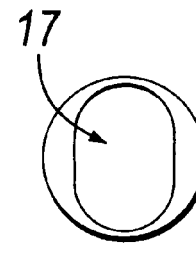
Figure 7:
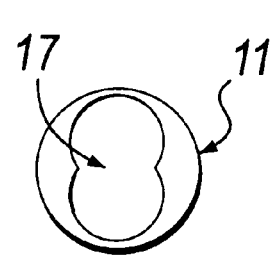
Figure 8:
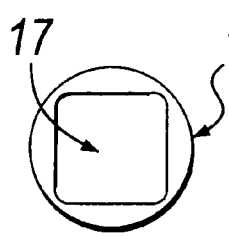
Figure 9:
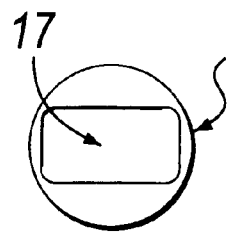
Figure 10:
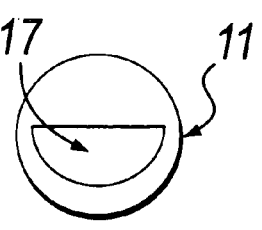

The hole 17 further has, depending on the type of use, a straight wall shape (see FIG. 1), or a shape that tapers from the outside toward said incision region (which corresponds to the bone to be cut), as shown in FIGS. 3 and 4; in this last case, the hole 17 having a circular cross-section has a substantially conical shape, preferably a straight conical shape.

The template 10 also comprises a jacket 20 that acts as a reference for the guiding body 11 and is designed to be rigidly fixed, by way of a supporting structure 21, at the incision region 15.

The jacket 20 has a through hole 22 that is formed by an internal surface 23 that is shaped complementarily to the lateral surface 14 of the guiding body 11 and is therefore cylindrical.

In particular, in this embodiment the jacket 20 has an outer surface 24 that has a substantially cylindrical shape.

Advantageously, on the outer surface 24 of the jacket 20 there is a first annular groove 25 to allow the jacket 20 to grip a supporting matrix 26 provided on the supporting structure 21 arranged in the incision region 15.

A second annular groove 27 is formed at an outer region of the lateral surface 14 of the guiding body 11 to allow to grip the supporting matrix if the guiding body 11 is applied without the jacket 20, as explained hereinafter.

The use of the template is as follows.

Consider for example the case of the execution of an osteotomy site for the insertion of a dental implant.

After determining the position in which the site is to be provided on the alveolar bone of the patient, an impression tray of the dental arch is performed.

The supporting structure 21 for the template 20 is provided by using the spatial references of said impression tray; said template is therefore positioned in the correct location for providing the site.

A matrix of resin 26 is arranged on the supporting structure 21 and stably locks the template 20 in position.

In particular, the jacket 20 is embedded in the matrix 26.

The guiding body 11 is inserted in the hole of the jacket so as to rest one end face of the guiding body on the bone to be cut.

At this point, the laser tip 12, which protrudes from the laser head 12a of a laser scalpel, is inserted in the hole 17.

The laser tip 12 must follow the internal surface of the hole 17 so as to provide the contour of the site.

The depth of the site is ensured by the fact that the height of the guiding body 11 is known and so is the length of the laser tip; at the most, the laser head can rest against the edge of the guiding body, thus ensuring the chosen depth of incision.

For this reason, guiding bodies having different heights and optional internal tapers are provided according to a series of predefined sizes.

For example, it is possible to provide templates in which, depending on the length of the guiding body, a particular inclination of the internal surface of the hole 17 is associated; moreover, the laser tip may also be adjusted in order to assume certain preset lengths, thus increasing the adjustment of the incision depth.

Having a through hole with an internal taper on the guiding body allows to provide conical sites.

The various shapes of the hole of the guiding body cited above (which can be tapered or not), allow to provide sites of an appropriate shape.

For example, the figure-of-eight shape is typical of the implantation of a molar, the triangular shape is typical of a canine, the ellipsoidal shape is typical of a premolar, and so forth; in this manner, it is possible to provide sites that comply with the original anatomy of the affected region.

It is extremely advantageous to use a jacket that is fixed in the matrix and a removable guiding body; in this manner one has great flexibility in choosing the sizes for providing the site. One can for example decide to use at the last minute, before the operation, a guiding body that is different from the preset one, since it is believed to be more suitable after visual assessment "in the field"; in this manner, one avoids having to remake the supporting structure.

Moreover, it is possible to recover the guiding body once the operation has been completed and to discard only the jacket embedded in the matrix of the supporting structure, said jacket being associable with all the models of various sizes of the guiding body.

The use of said template may be the most disparate, from the above described provision of osteotomy sites for dental implants to the calibrated removal of bone portions in various parts of the body for the most disparate reasons, biopsies, removal of material to be used in other regions, et cetera.

In practice it has been found that the invention thus described achieves the intended aim and objects; in particular, the present invention provides a shape and depth template for incisions with laser tips, particularly usable in bone surgery, that allows to provide osteotomy sites and bone samples having precise shapes and dimensions.

The invention thus conceived is susceptible of numerous modifications and variations, all of which are within the scope of the appended claims; all the details may further be replaced with other technically equivalent elements.

In practice, the materials used, as well as the contingent shapes and dimensions, may be any according to requirements and to the state of the art.

The disclosures in Italian Patent Application No. PD2003A000102 from which this application claims priority are incorporated herein by reference.

What is claimed is:

1. A shape and depth template for incisions with laser tips in bone surgery, comprising:
   a guiding body for guiding a laser tip, said guiding body being delimited by two mutually opposite end faces arranged at a preset distance and by a lateral surface, a tissue-contacting one of said end faces being arrangeable so as to rest on a region where incision is to be performed, by a laser tip said guiding body having a hole that passes through the guiding body from one of said end faces to the opposite one and that has a preset shape providing a contour to be followed by said laser tip;
   a jacket that forms a reference for said guiding body, said jacket comprising a first end surface, a mutually opposite second end surface, which surrounds said tissue contacting end an outer surface and a through hole formed by an internal surface thereof that is shaped complementarily to said lateral surface; and
   a supporting structure having an inner engaging structure which surrounds the second end surface, which is shaped complementarily to said outer surface at said second end surface, and which is shaped to contact substantially all of said jacket at said region and to enable rigid fixation of said jacket where laser tip incision is performed in an orientation such that said second end surface and said tissue-contacting end face are both held to rest upon the region, said supporting structure further having a perimeter extending radially outwardly from the engaging structure and oriented to fit over tissue surrounding the region.

2. The template of claim 1, further comprising surface indentations on said lateral and outer surfaces.

3. The template of claim 2, wherein said internal surface of said through hole of said jacket and said lateral surface of said guiding body are substantially cylindrical.

4. The template of claim 2, wherein said hole is shaped so as to taper from one end face of the guiding body toward the opposite end thereof where said laser tip incision region lays.

5. The template of claim 4, wherein said hole has a substantially straight conical shape.

6. The template of claim 2, further comprising a first annular groove formed on an outer lateral surface of said jacket.

7. The template of claim 6, further comprising a second annular groove formed at an outer region of said lateral surface of said guiding body.

8. The template of claim 1, wherein said hole is substantially straight wall shaped.

9. The template of claim 1, wherein said hole has a substantially circular cross-section.

10. The template of claim 1, wherein said hole has a substantially ellipsoidal cross-sectional shape.

11. The template of claim 1, wherein said hole has a substantially figure-of-eight cross-sectional shape.

12. The template of claim 1, wherein said hole has a substantially semicircular cross-sectional shape.

13. The template of claim 1, wherein said hole has a substantially triangular cross-sectional shape with radiused corners.

14. The template of claim 1, wherein said hole has a substantially square cross-sectional shape with radiused corners.

15. The template of claim 1, wherein said hole has a substantially rectangular cross-sectional shape with radiused corners.

* * * * *

UNITED STATES PATENT AND TRADEMARK OFFICE
CERTIFICATE OF CORRECTION

PATENT NO.      : 7,615,047 B2                                Page 1 of 1
APPLICATION NO. : 10/843476
DATED           : November 10, 2009
INVENTOR(S)     : Berna et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1218 days.

Signed and Sealed this

Nineteenth Day of October, 2010

David J. Kappos
*Director of the United States Patent and Trademark Office*